United States Patent [19]

Nieuwenhuis

[11] Patent Number: 5,442,058
[45] Date of Patent: Aug. 15, 1995

[54] CONVERSION OF PENICILLINS AND CEPHALOSPORINS TO 1-(S)-SULFOXIDES

[75] Inventor: Paulus G. J. Nieuwenhuis, Bathmen, Netherlands

[73] Assignee: Akzo Nobel N.V., Arnhem, Netherlands

[21] Appl. No.: 844,667

[22] PCT Filed: Sep. 27, 1990

[86] PCT No.: PCT/EP90/01643

§ 371 Date: Apr. 9, 1992

§ 102(e) Date: Apr. 9, 1992

[87] PCT Pub. No.: WO91/05788

PCT Pub. Date: May 2, 1991

[30] Foreign Application Priority Data

Oct. 16, 1989 [EP] European Pat. Off. ........... 89202606

[51] Int. Cl.[6] ................... C07D 501/02; C07D 499/04
[52] U.S. Cl. ................... 540/314; 540/215; 540/222; 540/228; 540/310; 540/312; 540/230
[58] Field of Search ............... 540/222, 215, 228, 310, 540/316, 312, 230

[56] References Cited

U.S. PATENT DOCUMENTS 3,275,626  9/1966  Morin et al. ................. 260/243

FOREIGN PATENT DOCUMENTS

| 0137534 | 4/1985 | European Pat. Off. . |
| 2552159 | 7/1976 | Germany . |
| 48-08795 | 2/1973 | Japan . |
| 51-056484 | 11/1974 | Japan . |
| 52-111587 | 9/1977 | Japan . |
| 61-050986 | 3/1986 | Japan . |
| 7309918 | 1/1974 | Netherlands . |
| 1594271 | 7/1981 | United Kingdom . |
| WO8503294 | 8/1985 | WIPO . |

OTHER PUBLICATIONS

Micetich, R. G., *Synthesis*, pp. 264–265 (1976).
Castellvi et al AFINIDAD XLIII, 406 pp. 505–507 1986.
Chemical Abstracts vol. 92 110912b (1980).
"Chemistry of Cephalosporin Antibiotics. Transformations of Penicillin Sulfoxide, A Synthesis of Cephalosporin Compounds" *J. Am. Chem. Soc.* vol. 91 No. 6, pp. 1401–1407 (1969).
Mangia, A., "A Mild and Convenient Synthesis of Penicillin and Cephalosporin Sulfoxides", *Synthesis*, pp. 361–363 (1978).
Guddal, E., et al, *Tetrahedron Letters*, No. 9, p. 381 (1962).
"Oxidation of Penicillin and Dihydrocephalosporin Derivatives with Ozone" *J. Org. Chem.* vol. 37, No. 5, p. 793 (1972).
"Conversion of Penicillin to Cephalosporin via a Double Sulfoxide Rearrangement" pp. 5006–5011, *J. Am. Chem. Soc.* (1970), vol. 92, Spry, D. O.
"Improvements In The Penicillin–Cephalosporin Transformation" Gruszecki, W. et al., Symp. Chem. Nat. Prod., 11th, (1978), 3, pp. 44–46.
Naponen, A., "Chem. Eng. News", Feb. 21, 1977, p. 5.
Flynn, Edwin H., "*Cephalosporins and Penicillins,*" Academic Press, pp. 185–214, 1972.

Primary Examiner—Nicholas Rizzo
Attorney, Agent, or Firm—Ralph J. Mancini; Louis A. Morris

[57] ABSTRACT

The present application discloses a process for the conversion of penicillin-1-(R)-sulfoxide(s) and/or cephalosporin-1-(R)-sulfoxides in solution, to their corresponding 1-(S)-sulfoxides comprising the step of treating said 1-(R)-sulfoxide with a sufficient amount of an acid anhydride to convert at least some of said 1-(R)-sulfoxide to its corresponding 1-(S)-sulfoxide. Also disclosed is a process for the production of 1-(S)-sulfoxide from penicillin and/or cephalosporin by oxidizing the penicillin or cephalosporin with an oxidizing agent and simultaneously or subsequently adding a sufficient amount of an acid anhydride to convert at least some 1-(R)-sulfoxide to its corresponding 1-(S)-sulfoxide over a time period of from 5 minutes to 2 hours so as to maintain the pH above 3.5 and produce a solution of the corresponding 1-(S)-oxide. In a preferred embodiment, a buffer is incorporated in the solution to provide additional pH control during the reaction. The process produces exceptionally high yields of high purity 1-(S)-oxides and is safer than most commercial processes which require the use and handling of 40% peracetic acid.

8 Claims, No Drawings

CONVERSION OF PENICILLINS AND CEPHALOSPORINS TO 1-(S)-SULFOXIDES

The present invention relates to a process for the conversion of the 1-(R)-sulfoxides of penicillin and cephalosporin to their corresponding 1-(S)-sulfoxides by treating said 1-(R)-sulfoxides with acid anhydride. The process is carried out in a aqueous medium in a temperature range from −15° to 30° C., the pH of said aqueous medium being maintained between 3.5 and 8. The process may be used to obtain high yields of substantially pure 1-(S)-sulfoxides from various grades of penicillin and cephalosporin at low cost and using shorter reaction times than present processes.

Penicillin-1-(S)-sulfoxide is an intermediate in the synthesis of cephalosporins as is known from R. B. Morin, et al., *J. Am. Chem. Soc.* 91, 1401 (1969). Penicillin-1-(S)-sulfoxide is commercially produced by the oxidation of natural Penicillin in aqueous medium with commercially available 40% peroxyacetic acid. For example, a procedure is described in, "A Convenient Synthesis of Ampicillin Sulfoxide and 6-Aminopenicillanic Acid Sulfoxide," Micetich, R. G., Synthesis, pp. 264–65 (1976) wherein peroxyacetic acid is employed to produce penicillin sulfoxides in aqueous solutions. However, such preparation processes are costly and extremely dangerous as is evidenced by the communication of A. Noponen, *Chem. Eng. News*, 21/2/77, p. 5, where Dr. Naponen reported a violent explosion during the preparation of 6-aminopenicillanic acid sulfoxide using the Micetich procedure. Further, the handling of peroxyacetic acid itself is a dangerous task.

Cephalosporin sulfoxides may also be used to produce other useful products as is disclosed in published European Patent Application 0 137 534, for example.

In, A. Mangia, "A Mild and Convenient Synthesis of Penicillin and Cephalosporin Sulfoxides," Synthesis, pp. 361–63 (1978), a number of synthetic methods for preparing penicillin sulfoxides are mentioned. Penicillin sulfoxides, for example, have been prepared by oxidation of penicillins with sodium periodate, ozone, m-chloroperbenzoic acid, and 40% peracetic acid. Although the yields were high, the reagents were expensive or troublesome to handle in large quantities. This communication further states that oxidation with hydrogen peroxide employed along with an organic acid in a large excess had been tried, but often this method led to cleavage of the more sensitive substrates with consequent low yields. The yields are evidenced by, E. Guddal, P. Morch and L. Tybring, Tetrahedron Lett., p. 381 (1962) wherein yields of 34–62% were obtained.

An alternative method of oxidizing penicillin to penicillin sulfoxides with hydrogen peroxide is also suggested in, A. Mangia, Synthesis, pp. 361–3 (1978) wherein the oxidation is carried out in dichloromethane solvent in the presence of a 4 molar excess of acetic or formic acid. However, this reaction suffers from the disadvantage of requiring reaction times of at least 9 hours and the use of an organic solvent which must be subsequently separated from the desired product at great cost and with extreme care in order to preserve the final product in unaltered form.

A similar reaction is suggested by Japanese Patent Application JP 51/56484 published on 18 May 1976, In this reaction, penicillin-(S)-oxides are prepared by oxidizing penicillin with hydrogen peroxide in the presence of maleic anhydride. The reaction requires that the penicillin and maleic anhydride be dissolved in trichloromethane and that a specific form of nitrated penicillin be employed for the reaction. In addition, this reaction is somewhat dangerous due to the addition of the hydrogen peroxide to a solution containing substantial amounts of maleic anhydride which results in the production of large amounts of peroxymaleic acid, used as the in situ generated oxidation agent, in the reaction medium.

A method for the oxidation of penicillin G to penicillin-G-1-(S)-oxide is disclosed in Castellvi and Coil, Afinidad XL 111,406, November-December 1986, wherein the potassium salt of penicillin G is oxidized with hydrogen peroxide in the presence of a tungsten or molybdenum catalyst. Several possible synergistic agents for these catalysts are also disclosed including sodium acetate, sodium nitrate, sodium chloride, sodium bromide, sodium fluoride, and sodium chlorate. In general, low yields are obtained using metal-assisted oxidation with hydrogen peroxide as is shown in JP 52/111587 published on 19 Sep. 1977 wherein a yield of only about 70% was obtained, and JP 48/8795 published on 3 Feb. 1973 wherein a yield of only about 89% was obtained. Further, degradation products of the penicillin G or the penicillin-G-1-(R) or (S)-oxides may form metal complexes with the metal catalysts which lead to contamination of the final products.

U.S. Pat. No. 3,275,626 also discloses a method for the oxidation of penicillin to penicillin sulfoxide by reacting penicillin V potassium salt with sodium metaperiodate in aqueous solution to produce penicillin V sulfoxide over a period of about 45 minutes.

WO 85/03294 discloses a method for the oxidation of penicillin V to penicillin V β-sulfoxide in a two-phase liquid system comprising hydrogen peroxide aqueous solution and an organic solvent or mixture of organic solvents.

However, this process suffers from the disadvantage that it takes 6–24 hours, probably because of the long time period required to crystallize the sulfoxides out of solution. Dutch patent application number 7,309,918 also discloses a method for the oxidation of penicillins and cephalosporins to their corresponding sulfoxides. This patent discloses the formation of the 1-(R)-sulfoxides and their structure. See also D. O. Spry, J. Org. Chem, 37, 793 , (1972) and J. Amer. Chem. Soc., 92, 5006 (1970).

Japanese patent application JP 61/050986, published on 13 Mar. 1986, discloses a process for the preparation of sulfoxides of penicillins and cephalosporins by oxidizing the penicillin or cephalosporin with hydrogen peroxide in the presence of phosphoric acid and, optionally a L reaction accelerator which may be an aromatic carboxylic acid anhydride. The role of this accelerator is probably the in situ generation of peroxycarboxylic acid, a strong oxidizing agent, by reaction with the hydrogen peroxide.

DE 25 52 159 discloses a process for the oxidation of penicillin esters to penicillin sulfoxide esters by reacting the penicilin esters with hydrogen peroxide in the presence of acid anhydride in a non-aqueous medium at a temperature of from −20° to 20° C. This process suffers from the disadvantage that the hydrogen peroxide is added to a mixture containing acid anhydride and a penicillin ester, which can produce dangerous levels of peroxy acids in the mixture. Further, the patent only exemplifies the oxidation of penicillin esters.

Patent GB 1,594,271 discloses the preparation of a 1-sulfoxide from peniciline or cephalosporin, preferably 1-(R)-sufoxide. The compound is treated in solution in a solvent selected from halogenated and monocyclic aromatic hydrocarbons with an oxidizing agent. This reaction gives a mixture of 1-(R)-and 1-(S)-sulfoxide or 1-(R)-sulfoxide as a major compound.

Finally, in Gruszecki W. et al., "Improvements in the penicillin-cephalosporin transformation", Symp. Pap. IUPAC Int. Symp. Chem. Nat. Prod., 11th 1978, 3, 44–46, a method is disclosed to oxidize penicillin esters to their sulfoxides by reacting the esters in a reaction medium of 30% hydrogen peroxide and acetic anhydride. However, the acetic anhydride is not dosed into the solution, neither are pH criteria disclosed, nor the yield of the (R)- or (S)-sulfoxides of penicillin esters.

The present invention has for its object to eliminate the shortcomings of the foregoing processes by providing a safe, economical process for the conversion of the undesirable 1-(R)-sulfoxides of penicillin and cephalosporin to their corresponding, desirable 1-(S)-sulfoxides and also provides a process for the production of high yields of substantially pure 1-(S)-sulfoxides of penicillin and cephalosporin from various forms of penicillins and cephalosporins. The processes are carried out in an aqueous medium at a temperature between −15° C. and 30° C., the pH of said aqueous medium being maintained between 3.5 and 8. These and other objects of the present invention will be apparent from the summary and detailed description which follow.

In its broadest aspect, the present invention relates to a process for the conversion of the 1-(R)-sulfoxides of penicillin and cephalosporin to their corresponding 1-(S)-sulfoxides by treating the 1-(R)-sulfoxides with an acid anhydride. The acid anhydride is dosed into an aqueous solution of the 1-(R)-sulfoxide of penicillin or cephalosporin in a sufficient quantity to effect the conversion of at least some of the 1-(R)-sulfoxide to the corresponding 1-(S)-sulfoxide. The process is carried out in an aqueous medium at a temperature between −15° C. and 30° C., the pH of said aqueous medium being maintained between 3.5 and 8. Dosing times may vary from about 1 minute to 2 hours depending upon the reactant concentrations and reaction conditions. Of course, shorter dosing times are preferred in order to keep the reaction short and dosing times of 5–20 minutes may provide high purity products in good yields.

The preferred acid anhydrides are those derived from aliphatic carboxylic acids. Acetic anhydride is the most preferred anhydride reactant. The acid anhydride is generally employed in a molar ratio to the 1-(R)-sulfoxide of penicillin or cephalosporin of from 0.05 to 4.0, and more preferably, 0.5 to 3.0.

In order to minimize the formation of undesirable by-products, operation of the conversion reaction at a pH above 3.5 is preferred. More preferably, the pH is maintained above 4.0 to thereby give the highest yields of 1-(S)-oxide. On the other hand, the pH levels above 8 will also lead to the formation of some undesirable by-products during the conversion process. Thus, the process is operated at pH levels between 3.5 and 8. The most preferred range for the operation of the present process is a pH of 4–5.

The reaction temperature must be high enough to prevent freezing the reaction media and low enough to provide reaction products of acceptable purity. The reaction temperature is not critical and may be from −15° C. to 30° C. and is more preferably from about 0°–5° C. At temperatures above about 30° C., significant decomposition of the penicillin or cephalosporin may occur, thereby contaminating the reaction products with undesirable decomposition products.

Initially, the 1-(S)-oxide reaction product will be formed in the reaction solution. It can be isolated from the solution in a purity of almost 100% by acidification of the solution with, for example, a strong mineral acid. Alternatively, additional reactions may be carried out on the 1-(S)-oxide while it remains in solution to produce other desired products.

Of course, any 1-(R)-sulfoxides of penicillins or cephalosporins may be converted by the process of the present invention, independent of the method used to produce the materials.

The present invention also relates to a process for the preparation of penicillin-1-(S)-sulfoxide from penicillin and cephalosporin-1-(S)-sulfoxide from cephalosporin, said process carried out at a temperature between −15° C. to 30° C., comprising the steps of preparing an aqueous solution of a compound selected from cephalosporin and penicillin, and 1.1 to 7 moles of an oxidizing agent per mole of said compound and simultaneously or subsequently adding a sufficient amount of an acid anhydride to the aqueous solution to convert any 1-(R)-sulfoxide formed by the oxidation reaction to its corresponding 1-(S)-sulfoxide to thereby produce a solution of the 1-(S)-oxide of said compound, said reaction solution having a pH between 3.5 and 8.0, optionally maintained through the use of a buffer.

In accordance with the present invention there is provided a simple process for the industrial-scale preparation of penicillin-1-(S) oxide by the oxidation Of the readily available forms of penicillin. The process provides exceptionally good yields which may be greater than 95% and, at the same time, is easy to carry out and intrinsically safe in operation. Further, the reagents used in the process are required in minimal quantities and are relatively inexpensive when compared with other reagents used in the oxidation of penicillin. The present process is also applicable to cephalosporin and is useful particularly in the purification of cephalosporins since impurities are more easily separated from the sulfoxide form of the cephalosporins. Plus, cephalosporin sulfoxides are useful as intermediates for the functionalization of desacetoxy cephalosporins.

The present process also provides the significant advantage that the 1-(S)-sulfoxide end product is easily isolated from the reaction media in an extremely pure form. This is the case even when industrial grade reactants are employed as the starting material. Finally, the present process enables the conversion of any penicillin-1-(R)-sulfoxide or cephalosporin-1-(R)-sulfoxide which is formed during the course of the reaction to the 1-(S)-sulfoxide form.

Penicillin sulfoxides, including penicillin-1-(S)-sulfoxide, are key reactive intermediates in the chemical manipulation of penicillins and can be employed to produce a host of useful derivative products. These sulfoxides are especially useful in the purification of industrial products as well as the in the production of cephalosporins. In the synthesis of cephalosporins it is of great economic advantage to oxidize natural penicillin G, one of the most readily available and least expensive naturally occurring penicillins, into its corresponding 1-(S)-oxide and then to esterify the oxide to produce the desired product, particularly in view of the high yields and exceptional purity of the penicillin-G-1-(S)-oxide obtained by the process of the present invention.

In the process of the present invention, an aqueous solution of penicillin or cephalosporin is prepared. The concentration of the solution may vary depending upon the desired reaction conditions, but is usually from 15 to 60% w/v. An oxidizing agent is also incorporated into this aqueous solution. The oxidizing agent is preferably added in the form of an aqueous solution having a concentration of 3–70% w/w. In actual practice, extremely dilute solutions of oxidizing agent on the order of 3–6% are generally employed for safety reasons. The oxidizing agent is preferably added to provide a molar ratio of oxidizing agent to penicillin or cephalosporin of from 1 to 7.

Suitable oxidizing agents useful in the process of the present invention include most conventional oxidizing agents such as hydrogen peroxide, sodium periodate, potassium persulfate, peroxycarboxylic acids such as peroxyacetic acid and m-chloroperoxybenzoic acid, ozone and other oxidizing agents. The particular oxidizing agent employed is not important and may be chosen on the basis of considerations such as cost and safety.

The penicillin or cephalosporin used in the process of the present invention may be any one or more of the forms of penicillin and cephalosporin including penicillin G, cephalosporin G, penicillin V, cephalosporin V, penicillin esters and cephalosporin esters, among others. Industrial grade or specialized materials having relatively high biological activity may be employed. Lower amounts of the acid anhydride and optional buffer may be employed when material having a high biological activity is used as a starting material. The penicillin or cephalosporin employed to make the aqueous solution is often in the form of a salt such as a sodium or potassium salt. The form of the cephalosporin or the penicillin, in this respect, does not affect the reaction in a significant way and thus may be chosen based on independent considerations. Thus, when making a solution of either penicillin or cephalosporin in accordance with the process of the present invention the pure form of the compound or a salt may be employed so long as the result is an aqueous solution containing pencillin or cephalosporin.

The pH of the reaction medium is maintained between about 3.5 and 8.0 in order to prevent the formation of undesirable by-products during the reaction. More preferably, the pH is kept at 4.0 to 5.0.

In the most preferred embodiment of the invention a buffer is added to the solution of penicillin or cephalosporin, and oxidizing agent, before the acid anhydride is dosed thereto. The buffer provides an excellent method for controlling the pH of the reaction medium during the addition of the acid anhydride and, in this manner, can be employed to optimize the reaction and produce the highest possible yields. In addition, it is thought that the buffer can act to increase the rate of reaction though the inventors do not wish to be bound by this theory.

The preferred buffers are alkali metal salts derived from weak acids. More preferred are the alkali earth metal salts of carboxylic acids although salts of inorganic acids are also useful. In some instances, the use of salts having the same negative ionic complex as the acid anhydride is desirable to prevent the introduction of additional ions into the reaction solution. However, any material which is known to provide buffer action in the pH range of 3,5 to 8 and does not adversely interfere with the basic reaction may be employed in the present process. The buffer is normally used in a concentration of from 0.1 to 30% w/v. Examples of suitable buffers include sodium and potassium acetates and carbonates and bicarbonates as well as sodium and potassium phosphates.

Also a part of the present production process is the above-described conversion of the formed 1-(R)-sulfoxides to the 1-(S)-sulfoxide form by the addition of an acid anhydride to the reaction medium. The acid anhydride treatment step may be carried out simultaneously with the oxidation step by simultaneous addition of acid anhydride and oxidizing agent, or the acid anhydride may be added after the oxidizing agent. It is generally preferable to add the acid anhydride to the reaction medium gradually over a period of from 1 minute to 2 hours and more preferably over a period of 5–20 minutes.

As stated above, it is preferable to control the pH throughout the reaction and that includes the conversion step with the acid anhydride. Of course, the resulting solution of 1-(S)-sulfoxide may be acidified in order to isolate the 1-(S)-sulfoxide by precipitation from solution.

The following examples of the present invention are provided for purposes of illustration and description only and are not to be construed as limiting the invention to the precise forms exemplified. The scope of the invention is to be determined from the claims appended hereto.

EXAMPLE 1

To a stirred solution of 37.2 grams (94.6 mmol) of penicillin G potassium salt (1590 units/mg, approx. 94.6%), 9.8 g. (100 mmol) potassium acetate and 0.2 g. of acetic acid in about 100 ml demi water, was added 9.5 g. (140 mmol) hydrogen peroxide (50%) at about 2° C. After stirring for about 5 minutes, 14.3 g. (140 mmol) of acetic acid anhydride was dosed into the solution over a period of 60 minutes at a temperature of about 2°–5° C. and a pH minimum of 4.8. A thin layer chromatogram indicated that substantially all of the starting material was converted. Analysis by 'H-NMR showed complete conversion into penicillin (S) sulfoxide. The pH of the solution was then lowered to 1.0 with 50 ml of 2 N and 100 ml of 1 N hydrochloric acid at about 2° C. over a period of 1 hour to form a precipitate. The precipitate was collected after another hour of stirring at 0° C. The filtercake was washed four times with ice-water (10 ml) and the white product was dried at ambient temperature to give 34.5 g. of penicillin (S) sulfoxide corresponding to a 95.3% yield.

EXAMPLES 2–7

Example 1 was repeated with and without the potassium acetate buffer and with variations in the relative amounts of reactants used. The amounts of reactants and results are shown in table 1.

EXAMPLE 8

Example 1 was repeated with the addition of potassium hydroxide simultaneously with the acetic anhydride to maintain the pH at a level of 5–7 throughout the reaction. The results of this example are also shown in table 1.

TABLE 1

Sulfoxidation of Penicillin G Potassium salt with hydrogen peroxide and acetic acid anhydride in aqueous medium at about 0° C.

| | Example | | | | | | | |
|---|---|---|---|---|---|---|---|---|
| | 1 | 2 | 3 | 4 | 5 | 6 | 7 | 8 |
| Starting Pen G K | | | | | | | | |
| Units/mg | 1590 | 1320 | 1320 | 1590 | 1590 | 1595 | 1595 | 1590 |
| conc. mol/l water | 0.9 | 0.9 | 0.9 | 1.0 | 1.0 | 1.0 | 1.0 | 0.9 |
| intake g | 37.2 | 37.2 | 37.2 | 18.6 | 18.6 | 18.6 | 18.6 | 37.2 |
| Potassium acetate mol/mol Pen G K | 1.0 | 1.0 | 1.0 | 1.0[1] | 0.1 | 0.0 | 0.0 | 0.0[2] |
| Reagents mol/mol Pen G K | 1.4 | 1.1 | 1.4 | 1.4 | 1.4 | 1.4 | 1.4 | 1.4 |
| Dosing time (min) acet. acid anhydr. | 60 | 16 | 55 | 15 | 15 | 10 | 60 | 25 |
| Final pH | 5 | 5 | 5 | 5 | 4 | 4 | 4 | 5 |
| Analysis intermediate (S)-sulfox. mol % (H-NMR) | >95 | ~80 | >95 | >95 | ~95 | ≈95 | ≈90 | ≈80 |
| Weight yield g, | 34.5 | 30.9 | 28.3 | 16.9 | 16.4 | 17.5 | 16.6 | 29.5 |
| Analysis final product: | | | | | | | | |
| Water content % | 8.5 | 2.3 | 2.4 | 8.6 | 2.7 | 7.0 | 3.1 | 8.5 |
| (S)-sulfox. mol % (H-NMR) | ≈100 | ≈80 | ≈100 | ≈100 | >95 | >95 | >95 | ≈100 |
| Chemical yield % based on Int. Stand 1598 units/mg | 90.7 | ≈84 | 95.4 | 88.6 | <92 | <93 | <92 | 77.5 |
| based on USP max. 1680 units/mg | 95.3 | ≈88 | 100 | 93.2 | <96 | <98 | <97 | 81.5 |

[1] added simultaneously
[2] potassium hydroxide added simultaneously

Comparative Example 1

Example 1 was repeated with a reversed order of reactant addition, i.e. first acetic acid anhydride then hydrogen peroxide and in the presence of potassium bicarbonate buffer.

To a stirred solution of 37.2 grams of Pencillin G potassium salt (industrial grade) and 10.0 g (100 mmol) potassium bicarbonate in about 165 ml demi water was added 11.7 g (115 mmol) acetic acid anhydride over a period of 20 minutes at about 2° C. After stirring for about 5 minutes, 8.1 g (121 mmol) of hydrogen peroxide (50%) was dosed into the solution over a period of 30 minutes at a temperature of about 2°–4° C. and a pH minimum of 5.4. A thin layer chromatogram indicated that substantially all of the starting material was converted, but only partially into penicillin 1-(S)-oxide. Analysis by 'H-NMR showed only about 45% conversion into penicillin 1-(S)-oxide.

EXAMPLE 9

To demonstrate the action of acetic acid anhydride in the present invention the reaction product of comparative example 1 was treated by addition of 10.2 g (100 mmol) acetic acid anhydride over a period of 45 minutes at about 2°–5° C. and at a pH minimum of 4.8. A thin layer chromatogram indicated that substantially all of the starting material was convened into penicillin 1-(S)-oxide. Analysis by 'H-NMR showed nearly complete conversion into penicillin G-1-(S)-oxide.

The acidification procedure of Example 1 was then followed. The yield was 27.0 g(−70% wt) penicillin 1-(S)-oxide of high purity.

The foregoing examples have been provided for purposes of illustration and description only and are not to be construed as limiting the claims to the precise forms disclosed. The scope of the invention is to be determined by the claims appended hereto.

I claim:

1. A process for the conversion of a compound selected from the group consisting of 1-(R)-sulfoxide containing penicillins, cephalosporins and mixtures thereof, to the corresponding 1-(S)-sulfoxides, said process comprising the step of treating an aqueous solution comprising 1-(R)-sulfoxide containing penicillin, cephalosporin and mixtures thereof, with an amount of acid anhydride effective to convert said 1-(R)-sulfoxide to the corresponding 1-(S)-sulfoxide, said conversion process carried out at a temperature of between −15° and 30° C. and the pH of said aqueous solution being maintained between 3.5 and 8.

2. A process for the preparation of a 1-(S)-sulfoxide from at least one compound selected from the group consisting of penicillins and cephalosporins, in an aqueous medium, the pH of said aqueous medium being maintained between 3.5 and 8, and the process carried out at T=−15°–30° C., comprising the steps of:
   (a) oxidizing said compound in said aqueous media with 1.1 to 7 moles of an oxidizing agent per mole of said at least one compound; and
   (b) simultaneously or subsequently adding an effective amount of an acid anhydride to convert at least some 1-(R)-sulfoxide to 1-(S)-sulfoxide, to said a aqueous solution of said at least one compound over a time period of from 1 minute to 2 hours to produce a solution of primarily penicillin and/or cephalosporin 1-(S)-sulfoxide.

3. The process in accordance with claim 2 wherein said aqueous solution further comprises a buffer.

4. The process in accordance with claim 3 wherein said buffer is present in an amount sufficient to maintain the pH of the reaction mixture above 4.5 throughout the step of acid anhydride addition.

5. The process in accordance with any one of claims 1–4 wherein the amount of said acid anhydride is from 0.05 to 4.0 moles per mole of said 1-(R)-sulfoxide containing penicillin, cephalosporin and mixtures thereof.

6. The process in accordance with claim 5 wherein said acid anhydride is added gradually over a time period of between 5 minutes and 20 minutes.

7. The process in accordance with claim 6 further comprising the step of acidifying said solution of 1-(S)-oxide to crystallize the 1-(S)-oxide out of said solution.

8. The process of claim 5 wherein the 1-(R)-sulfoxide containing penicillin or cephalosporin is selected from the group consisting of penicillin G, cephalosporin G, penicillin V, cephalosporin V, penicillin esters, cephalosporin esters, and mixtures thereof.

* * * * *

UNITED STATES PATENT AND TRADEMARK OFFICE
CERTIFICATE OF CORRECTION

PATENT NO. : 5,442,058
DATED : August 15, 1995
INVENTOR(S) : Paulus G.J. Nieuwenhuis It is certified that error appears in the above—identified patent and that said Letters Patent is hereby corrected as shown below:

Column 8
In claim 2, line 3, "1-(R)-sulfoxide containing" should be inserted before "penicillins".

Signed and Sealed this

Nineteenth Day of December, 1995

Attest:

BRUCE LEHMAN

Attesting Officer

Commissioner of Patents and Trademarks